United States Patent
Soloveichik

(10) Patent No.: US 7,022,886 B2
(45) Date of Patent: *Apr. 4, 2006

(54) SELECTIVE CATALYTIC OXYBROMINATION OF HYDROXYAROMATIC COMPOUNDS

(75) Inventor: Grigorii Lev Soloveichik, Latham, NY (US)

(73) Assignee: General Electric Company, Schenectady, NY (US)

( * ) Notice: Subject to any disclaimer, the term of this patent is extended or adjusted under 35 U.S.C. 154(b) by 240 days.

This patent is subject to a terminal disclaimer.

(21) Appl. No.: 10/650,567

(22) Filed: Aug. 28, 2003

(65) Prior Publication Data

US 2005/0049441 A1 Mar. 3, 2005

(51) Int. Cl.
*C07C 39/24* (2006.01)
(52) U.S. Cl. .................................... 568/779
(58) Field of Classification Search ............. 568/779
See application file for complete search history.

(56) References Cited

U.S. PATENT DOCUMENTS

| | | | | |
|---|---|---|---|---|
| 3,987,068 A | * | 10/1976 | Reilly | 552/296 |
| 6,815,565 B1 | * | 11/2004 | Mills et al. | 568/779 |
| 2004/0143144 A1 | * | 7/2004 | Pressman et al. | 568/812 |

OTHER PUBLICATIONS

K-J Lee et al., "Bromination of Activated Arenes by Oxone® and Sodium Bromide", *Bull. Korean Chem. Soc.* 22 (5), 773-74 (2002).

R. Neumann and I. Assael, "Oxybromination Catalysed by the Heteropolyanion Compound $H_5PMO_{10}\ V_2O_{40}$ in an Organic Medium: Selective para-Bromination of Phenol", *J. Chem. Soc., Chem.Commun.*, 1285-87 (1988).

U. Bora et al., "Regioselective Bromination of Organic Substrates by Tetrabutylammonium Bromide Promoted by $V_2O_5O_2$-$H_2O_2$: An Environmentally Favorable Synthetic Protocol", *Org. Lett.*, 2 (3), 247-49 (2000).

K. Krohn et al., "Para-Selective Chlorination and Bromination of Phenols with tert-Butyl Hydroperoxide and TiX $(OiPR)_3$", *J. Prakt. Chem.* 341 (1), 59-61 (1999).

T. Oberhauser, "A New Bromination Method for Phenols and Anisoles: $NBS/HBF_4Et_2O$ In $CH_3CN$", *J. Org. Chem.* 62, 4504-06 (1997).

N. Narender et al., "Liquid phase bromination of phenols using potassium bromide and hydrogen peroxide over zeolites"; *Molec. Catalysis A: Chem.* 192, 73-77 (2003).

U.S. Appl. No. 10/342,475, filed Jan. 16, 2003, "Bromination of Hydroxyaromatic Compounds and Further Conversion to Dihydroxyaromatic Compounds".

BP Bandgar et al., "*Regioselective Catalytic Halogenation of Aromatic Substrates*", Synthetic Communications, vol. 28, No. 17, pp. 3225-3229, 1998.

Visnumurthy R. Hedge et al., "*Regioselective Catalytic Halogenation of Arenes, Mimicking Vanadium Haloperoxidase Reactions*", J. Chem. Research, pp. 62063, 1996.

James H. Espenson et al., "*Bromide ions and Methyltrioxorhenium as Cocatalysts for hydrogen Peroxide Oxidations and Brominations*", Journal of Organic Chemistry, vol. 64, pp. 1191-1196, 1999.

Search Report dated Dec. 28, 2004.

* cited by examiner

*Primary Examiner*—Michael L. Shippen
(74) *Attorney, Agent, or Firm*—Heslin Rothenberg Farley & Mesiti P.C.; Martha L. Boden

(57) ABSTRACT

A method for selectively brominating hydroxyaromatic compounds is disclosed. Hydroxyaromatic compounds are contacted with oxygen and a bromine source, in an acidic medium, in the presence of a catalyst selected from the group of compounds and mixtures of compounds of Group IV–VIII transition metals of the Periodic Table of Elements. The selectivity of mono-brominated products produced, predominantly in the para-position, from the method using transition metal compounds as catalysts is significantly higher than that of known methods using other catalysts. Thus, there is a significant reduction in the production of undesirable dibrominated and more highly brominated by-products.

26 Claims, No Drawings

US 7,022,886 B2

SELECTIVE CATALYTIC OXYBROMINATION OF HYDROXYAROMATIC COMPOUNDS

CROSS-REFERENCE TO RELATED APPLICATIONS

This Application is related to the following U.S. Patent Applications:

U.S. Ser. No. 10/342,475, filed Jan. 16, 2003, entitled "BROMINATION OF HYDROXYAROMATIC COMPOUNDS AND FURTHER CONVERSION TO DIHYDROXYAROMATIC COMPOUNDS"; and U.S. patent application Ser. No. 10/650,566, filed Aug. 28, 2003, entitled "BROMINATION OF HYDROXYAROMATIC COMPOUNDS".

Each of these Applications is hereby incorporated by reference herein in its entirety.

BACKGROUND OF THE INVENTION

This invention relates to the catalyzed bromination of hydroxyaromatic compounds, and more particularly to the use of transition metal compound catalysts for improved para- and mono-selectivity of the reaction products.

Monocyclic dihydroxyaromatic compounds such as hydroquinone and dihydroxybiphenyls such as 4,4'-dihydroxybiphenyl (hereinafter sometimes simply "biphenol") have numerous uses in the chemical industry. For example, both compounds can be used in polymer preparation, notably in the preparation of polycarbonates, polysulfones and polyimides, especially polyetherimides.

There are various methods for the preparation of hydroquinone and biphenol. As examples of such methods, each compound can be prepared from p-bromophenol: hydroquinone by hydrolysis: and biphenol by reductive coupling in the presence of a noble metal catalyst, a base and a reducing agent.

Brominated hydroxyaromatic compounds, as exemplified by p-bromophenol, can be prepared by reaction of the precursor hydroxyaromatic compound with HBr, elemental bromine, or with various kinds of bromides. Commonly assigned, co-pending U.S. application Ser. No. 10/342,475 (filed Jan. 16, 2003) discloses an efficient means of preparing brominated hydroxyaromatic compounds including p-bromophenol. The method comprises contacting a hydroxyaromatic compound with oxygen and a bromide source in an acidic medium, in the presence of elemental copper or a copper compound as catalyst.

While this approach provides additional efficiencies relative to other known methods, improved methods continue to be sought. In particular, it would be advantageous to reduce the formation of multi-brominated by-products, thereby increasing the selectively of the reaction to form predominantly mono-brominated products, especially those where substitution occurs in the para-position relative to the hydroxy group. Furthermore, because of the extremely high corrosiveness of copper salts in acid media, it would be advantageous if other catalysts could be used in the oxybromination of hydroxyaromatic compounds.

SUMMARY OF THE INVENTION

The present invention provides an efficient method for selectively brominating hydroxyaromatic compounds to form mono-substituted products while minimizing the formation of dibromo-phenols and more highly brominated by-products. In addition, the method provides high selectivity for producing para-brominated hydroxyaromatic compounds relative to ortho-brominated products. The method provides overall high process yields, as well as high selectivity, using transition metal compounds of Groups IV–VIII to catalyze the oxybromination reaction. Furthermore, corrosive copper catalysts need not be employed.

Therefore, in one aspect, the present invention relates to a method for preparing a brominated hydroxyaromatic compound. The method comprises contacting a hydroxyaromatic compound with oxygen and a bromine compound selected from the group consisting of hydrogen bromide, elemental bromine, ionic bromide salts, and mixtures thereof, in an acidic medium, in the presence of a catalyst selected from the group of compounds and mixtures of compounds of Group IV–VIII transition metals of the Periodic Table of Elements.

In another aspect, the invention relates to a method for preparing 4-bromophenol, 4-bromo-o-cresol or 4-bromo-m-cresol, which comprises contacting phenol, o-cresol or m-cresol, respectively, with air and hydrogen bromide in an acidic medium, in the presence of a catalyst selected from the group of compounds and mixtures of compounds of Group IV–VIII transition metals of the Periodic Table of Elements.

DETAILED DESCRIPTION OF THE PREFERRED EMBODIMENTS

The present invention relates to the novel use of compounds and complexes of Group IV–VIII transition metals to catalyze the selective oxybromination of hydroxyaromatic compounds. Unexpectedly, the products are mostly mono-brominated compounds, predominantly the p-bromo compound, with minor amounts of o-bromo compound being present. Formation of multi-brominated by-products is substantially reduced in comparison to prior methods, through the use of these catalysts.

The common initial reactant for all products obtained according to the method of this invention is a hydroxyaromatic compound, such as a monocyclic monohydroxyaromatic compound. The hydroxyaromatic compound is contacted with oxygen and a bromine compound in the presence of a catalyst, which is a compound or mixture of compounds of Group IV–VIII transition metals of the Periodic Table. The bromination reaction may be conducted at a temperature in the range of about 20–150° C., but generally about 60–100° C.

As used herein, "selectivity" to brominated products means moles of specific brominated products as a percentage of moles of hydroxyaromatic compound consumed. Furthermore, "monoselectivity" is defined herein as moles of para-brominated and ortho-brominated product formed as a percentage of moles of para-brominated products, ortho-brominated products, dibrominated products, and more highly brominated products formed. Selectivity to the p-brominated products, i.e. "paraselectivity" is defined as the percentage of mono-brominated products which are brominated in the para-position, the remainder of which are ortho-brominated compounds.

The hydroxyaromatic reactant may be an unsubstituted hydroxyaromatic compound such as phenol, or a substituted compound provided that the 4-position is unsubstituted and thus available for bromination. As one of skill would know, the 2-, 3-, and 4-positions relative to the carbon attached to the hydroxy group are also known as and referred to herein as ortho-, meta-, and para-, respectively. Furthermore, o- refers to ortho-; m- refers to meta-; and p- refers to para-. Note that a substituent may be located at any position of the aryl ring other than the 1- or 4-carbons. Exemplary substituents (one or more) are alkyl groups, particularly $C_{1-4}$ alkyl. Illustrative compounds are those having the formula

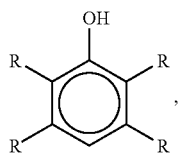

wherein each R is independently hydrogen or a substituent, preferably $C_{1-4}$ alkyl.

Particularly preferred in most instances is phenol, and specific reference will frequently be made to phenol hereinafter. However, homologous compounds such as o- and m-cresol may be substituted for phenol as desired.

The oxygen is employed in stoichiometric excess and may be pure oxygen or may be employed in the form of air or oxygen-enriched air. Contact may be made with flowing oxygen or air or under pressure, typically up to about 100 atm.

Suitable bromine compounds include hydrogen bromide, elemental bromine ($Br_2$), and bromide salts. Mixtures of the bromine compounds may also be used. Hydrogen bromide may be employed in any form; examples are gaseous HBr, aqueous HBr (hydrobromic acid) and HBr in solution in a polar organic solvent, typically one of the solvents described hereinafter. Often the starting reaction medium will be anhydrous. Bromide salts include alkali metal bromides such as sodium bromide and potassium bromide and alkaline earth metal bromides such as calcium bromide and magnesium bromide.

The contact is in an acidic medium. Aqueous acidic media including Bronsted acids generally, and particularly including sulfuric acid, phosphoric acid and triflic acid, may be employed; or, if hydrobromic acid is the bromine compound employed, it may also serve as the acidic medium. Polar solvents may also be present. These may include polar aprotic solvents such as acetonitrile, dimethyl sulfoxide, chloroform, ethyl acetate, and o-dichlorobenzene, as well as protic solvents such as water, acetic acid, propionic acid, and excess hydroxyaromatic compound. Acetic acid is frequently preferred. Mixtures of the foregoing solvents may also be employed. As previously mentioned, the reaction medium is frequently anhydrous.

Hydrogen bromide in acetic acid under anhydrous conditions or hydrobromic acid are generally preferred as bromine sources/acidic mediums. Hydrobromic acid may be employed at any concentration, including the commercially available 48% or 62% (by weight) aqueous solution. Acetic acid is also frequently added when hydrobromic acid is employed.

The molar ratio of ionic bromide to hydroxyaromatic compound is preferably less than 1:1, to minimize conversion to dibromo and more highly brominated compounds; ratios in the range of about 0.2–0.9:1 are typical. However, when elemental bromine is the bromide compound, the molar ratio of $Br_2$ to hydroxyaromatic compound is preferably less than 1:2, typically in the range of about 0.2–0.9:2, again to minimize the formation of by-products. As disclosed in copending, commonly owned U.S. patent application Ser. No. 10/650,566, filed Aug. 28, 2003, entitled "BROMINATION OF HYDROXYAROMATIC COMPOUNDS", one mole of bromine reacts with one mole phenol to generate 1 mole of p-bromophenol and 1 mole of HBr, which then reacts with a second mole of phenol in the presence of oxygen and the catalyst to yield a second mole of p-bromophenol. Thus, use of the catalysts described herein allows consumption of all the bromine employed in the bromination reaction using inexpensive oxygen, such as in air, as an oxidant.

The oxybromination reaction of the present invention occurs in the presence of a catalyst comprising one of more compounds or complexes of Group IV–VIII transition metals. A molar ratio of hydroxyaromatic compound to the catalyst ranging from about 1:1 to about 500:1 minimizes conversion of the products to dibromo and more highly brominated compounds. Typically, a molar ratio of 200:1 provides a high product yield with excellent mono-selectivity.

For use in the catalytic compounds, suitable Group IV–VIII transition metals include vanadium, titanium, molybdenum, tungsten, and iron, for example. However, the invention is not limited to compounds of these metals. With respect to vanadium, any vanadium source including cationic, anionic salts and neutral complexes may be used as the catalyst for selective oxybromination of phenolics. Vanadate salts, such as sodium metavanadate having the chemical formula $NaVO_3$, are preferentially used. Other catalysts which have proven useful for these bromination reactions include, for example, bis(acetylacetonate)oxovanadium, bis(acetylacetonate)oxotitanium, sodium molybdenum oxide dihydrate ($NaMoO_4 \cdot 2H_2O$), iron bromide ($FeBr_2$), and tungstic acid ($H_2WO_4 \cdot xH_2O$). Bis(acetylacetonate)oxovanadium has the chemical formula $VO(CH_3COCHCOCH_3)_2$, which is often abbreviated as $VO(acac)_2$. Likewise, bis(acetylacetonate)oxotitanium has formula $TiO(CH_3COCHCOCH_3)_2$, which is also referred to as $TiO(acac)_2$. However, the invention is not limited to use of these catalysts, and other ligands and salts will be obvious to those of skill.

In addition, the Group IV–VIII transition metal catalyst compounds may be used alone or in combination. For example, a mixture of any of the aforementioned catalysts may be employed. In one embodiment, a compound of vanadium mixed with a compound of molybdenum is employed as the catalyst. In another embodiment, the catalyst is a compound of vanadium mixed with a compound of tungsten. In general, a mixture of Group IV–VIII transition metal compounds often improves the selectivity of the reaction to brominated products and the paraselectivity. Furthermore, the yield of brominated products generally increases significantly, as does the rate of the reaction. The molar ratio of the vanadium compound to the other metal compound is in the range of about 1:0.5 to about 1:6. Examples of such combinations include mixtures of sodium metavanadate ($NaVO_3$) with either sodium molybdenum oxide dihydrate ($NaMoO_4 \cdot 2H_2O$) or tungstic acid ($H_2WO_4 \cdot xH_2O$).

In another embodiment of the present invention, a nitrate salt, such as sodium nitrate, may be added to the catalyst to improve performance and activity of the catalyst. Addition of a nitrate salt increases the yield of the mono-brominated product and the rate of the reaction, and in some embodiments the selectivity to brominated products and paraselectivity also improves. The molar ratio of the nitrate salt to the Group IV–VIII transition metal catalyst compound(s) preferably ranges from about 1:1 to about 1:4. However a ratio of about 1:2 is typical. Sodium nitrate in combination with a compound of vanadium will often be used to catalyze the reaction.

The addition of water to the reaction mixture when the reaction is run under anhydrous conditions influences the catalytic bromination. The addition of a small amount of water typically increases mono-selectivity, but the reaction rate and bromophenol yield noticeably decrease. Generally, when the bromine source is anhydrous HBr or an anhydrous ionic bromide salt, a molar ratio of water to bromine source ranging from about 0.1:1 to about 2:1 is effective.

As previously mentioned, the products of the catalytic bromination reaction are mostly mono-brominated compounds, predominantly in the para position, with minor amounts of compounds brominated in the ortho position being present. Formation of dibrominated and more highly brominated by-products is reduced using the Group IV–VIII transition metal catalysts described herein. Selectivity to brominated phenol products is generally greater than 79%, but typically ranges from 94–100% when a vanadium catalyst is employed. Furthermore, a monoselectivity of 100% is often observed, but frequently ranges from 96–100% depending on the reactants, catalyst(s), and reaction conditions used. However, a monoselectivity greater than 70% is acceptable. In addition, selectivity to the p-brominated products, i.e. "paraselectivity" is usually at least 80% and often greater than 90%.

The following examples are given by way of illustration and are not intended to be limitative of the present invention. The reagents, reactants, and catalysts used in the oxybromination reaction described herein are readily available materials. Such materials can be conveniently prepared in accordance with conventional preparatory procedures or obtained from commercial sources. As used herein, the term "Selectivity to BrPhOH" refers to the selectivity to monobrominated phenols following the catalytic bromination of phenol. "Yield of BrPhOH" refers to the yield of monobrominated phenol products.

Examples 1–6 illustrate the catalytic bromination of phenol with HBr aq/$O_2$ in a solvent using compounds of Group IV–VIII transition metals as the catalyst.

EXAMPLE 1

A 3-dram vial equipped with a stirring bar was charged with 1.5 g (15.9 mmol) phenol, 2.95 g of aqueous HBr (48 wt %) (17.5 mmol), 1.5 g of acetic acid, and 0.250 g (1.0 mmol) of VO(acac)$_2$. The vial was sealed with a cap containing a hole to allow for air flow during the reaction and placed in an aluminum block. The block was placed in a standard one gallon Autoclave Engineers autoclave reactor, pressurized to 34.0 atm with air and heated at 100° C. for 2 hours. It was then cooled to room temperature and depressurized. The resulting mixture was analyzed by vapor phase chromatographic analysis. The results are shown in Table I.

EXAMPLE 2

The procedure of Example 1 was followed except that the vial was charged with 1.5 g (15.9 mmol) phenol, 1.47 g of aqueous HBr (48 wt %) (8.72 mmol), 2.5 g of acetic acid, and 0.250 g (1.0 mmol) of VO(acac)$_2$. The results are shown in Table I.

EXAMPLE 3

The procedure of Example 1 was followed except that the vial was charged with 1.5 g (15.9 mmol) phenol, 2.0 g of aqueous HBr (48 wt %) (11.9 mmol), 1.5 g of acetic acid, and 0.175 g (0.7 mmol) of VO(acac)$_2$. The results are shown in Table I.

EXAMPLE 4

The procedure of Example 1 was followed except that the vial was charged with 1.5 g (15.9 mmol) phenol, 2.0 g of aqueous HBr (48 wt %) (11.9 mmol), 1.35 g of ethyl acetate, and 0.175 g (0.7 mmol) of VO(acac)$_2$. The results are shown in Table I.

EXAMPLE 5

The procedure of Example 1 was followed except that the vial was charged with 1.5 g (15.9 mmol) phenol, 2.0 g of aqueous HBr (48 wt %) (11.9 mmol), 1.35 g of ethyl acetate, and 0.107 g (0.5 mmol) of FeBr$_2$. The results are shown in Table I.

EXAMPLE 6

The procedure of Example 1 was followed except that the vial was charged with 1.5 g (15.9 mmol) phenol, 2.5 g of aqueous HBr (48 wt %) (14.8 mmol), 2.5 g of acetic acid, and 0.155 g (0.7 mmol) of NaMoO$_4 \cdot$2H$_2$O. Also, the vial was pressurized to 6.8 atm with air instead of 34.0 atm. The results are shown in Table I.

TABLE I

Catalytic Bromination of Phenol with HBr aq/O$_2$ in a Solvent

| Example | HBr aq, g | Solvent (g) | Catalyst (g) | Yield of BrPhOH % | Selectivity to BrPhOH % | Rate, mol/L · h | Para-selectivity % | Mono-selectivity % |
|---|---|---|---|---|---|---|---|---|
| 1 | 2.95 | C$_2$H$_5$COOH (1.5) | VO(acac)$_2$ (0.250) | 11.6 | 79.6 | 0.31 | 80.3 | 100 |
| 2 | 1.47 | C$_2$H$_5$COOH (2.5) | VO(acac)$_2$ (0.250) | 12.8 | 79.2 | 0.36 | 86.1 | 100 |
| 3 | 2.0 | C$_2$H$_5$COOH (1.5) | VO(acac)$_2$ (0.175) | 18.0 | 87.0 | 0.55 | 80.9 | 100 |
| 4 | 2.0 | CH$_3$COOEt (1.35) | VO(acac)$_2$ (0.175) | 6.5 | n/a | 0.21 | 84.6 | 100 |
| 5 | 2.0 | CH$_3$COOEt (1.35) | FeBr$_2$ (0.107) | 4.8 | n/a | 0.16 | 84.0 | 100 |
| 6 | 2.5 | CH$_3$COOH (2.5) | NaMoO$_4$ 2H$_2$O (0.155) | 3.3 | n/a | 0.1 | 79.3 | 100 |

As can be seen in Table I, compounds and complexes of Group IV–VIII transition metals selectively catalyzed the oxybromination of phenol to predominantly p-bromophenol. Furthermore, in a system containing aqueous HBr and acetic acid, conversion from phenol to the brominated products was very high, as indicated by "Selectivity to BrPhOH". Unexpectedly, the brominated phenols were entirely mono-brominated as either para-bromophenol or ortho-bromophenol. No dibromophenol or higher brominated by-products were produced. Paraselectivity ranged from 79.3–86.1%. Examples 7–15 illustrate the catalytic bromination of phenol with anhydrous HBr/O$_2$ in a solvent using compounds of Group IV–VIII transition metals as the catalyst.

EXAMPLE 7

The procedure of Example 1 was followed except that the vial was charged with 1.5 g (15.9 mmol) phenol, 4 g of 30 % solution of HBr (14.8 mmol) in acetic acid, and 0.174 g (0.7 mmol) of VO(acac)$_2$. Furthermore, the reaction was conducted for 1 hour at 100° C. instead of 2 hours. The results are found in Table II.

EXAMPLE 8

The procedure of Example 7 was followed except that 0.108 g (0.5 mmol) of FeBr$_2$ was added as the catalyst. The results are found in Table II.

EXAMPLE 9

The procedure of Example 7 was followed except that 0.131 g (0.5 mmol) of TiO(acac)$_2$ was added as the catalyst. The results are found in Table II.

EXAMPLE 10

The procedure of Example 7 was followed except that 0.155 g (0.7 mmol) of NaMoO$_4$.2H$_2$O was added as the catalyst. Also, the vial was pressurized to 6.8 atm with air instead of 34.0 atm. The results are found in Table II.

EXAMPLE 11

The procedure of Example 7 was followed except that 0.188 g (0.7 mmol) of H$_2$WO$_4$.xH$_2$O was added as the catalyst. Also, the vial was pressurized to 6.8 atm with air instead of 34.0 atm. The results are found in Table II.

EXAMPLE 12

The procedure of Example 7 was followed except that 0.155 g (0.7 mmol) of NaMoO$_4$.2H$_2$O was added as the catalyst. Also, the reaction was conducted for 2 hours at 65° C. instead of 1 hour at 100° C. The results are found in Table II.

EXAMPLE 13

The procedure of Example 12 was followed except that 0.188 g (0.7 mmol) of H$_2$WO$_4$.xH$_2$O was added as the catalyst. The results are found in Table II.

EXAMPLE 14

The procedure of Example 12 was followed except 0.174 g (0.7 mmol) of VO(acac)$_2$ was added as the catalyst. The results are found in Table II.

EXAMPLE 15

The procedure of Example 12 was followed except 0.026 g (0.1 mmol) of VO(acac)$_2$ was added as the catalyst. The results are found in Table II.

TABLE II

Catalytic Bromination of Phenol with Anhydrous HBr/O$_2$ in Acetic Acid

| Example | Catalyst (g) | Yield of BrPhOH, % | Selectivity to BrPhOH, % | Rate, mol/L · h | Para-selectivity, % | Mono-selectivity, % |
|---|---|---|---|---|---|---|
| 7 | VO(acac)$_2$ (0.174) | 54.2 | 88.4 | 1.53 | 67.9 | 92.4 |

TABLE II-continued

Catalytic Bromination of Phenol with Anhydrous HBr/O$_2$ in Acetic Acid

| Example | Catalyst (g) | Yield of BrPhOH, % | Selectivity to BrPhOH, % | Rate, mol/L · h | Para-selectivity, % | Mono-selectivity, % |
|---|---|---|---|---|---|---|
| 8 | FeBr$_2$ (0.108) | 6.9 | 15.3 | 0.20 | 63.9 | 79.1 |
| 9 | TiO(acac)$_2$ (0.131) | 13.6 | 27.6 | 0.38 | 66.2 | 96.2 |
| 10 | NaMoO$_4$.2H$_2$O (0.155) | 9.6 | 36.3 | 0.30 | 64.7 | 84.7 |
| 11 | H$_2$WO$_4$.xH$_2$O (0.188) | 9.6 | 31.3 | 0.30 | 64.0 | 71.2 |
| 12 | NaMoO$_4$.2H$_2$O (0.155) | 20.6 | 87.3 | 0.30 | 83.5 | 100 |
| 13 | H$_2$WO$_4$.xH$_2$O (0.188) | 16.4 | 62.9 | 0.23 | 82.1 | 98.1 |
| 14 | VO(acac)$_2$ (0.174) | 55.2 | 94.9 | 0.77 | 90.3 | 99.3 |
| 15 | VO(acac)$_2$ (0.026) | 53.8 | 95.7 | 0.76 | 87.5 | 99.3 |

Again, as indicated in Table II, monoselectivity of the brominated phenol was very high using the catalysts discussed herein in a system using anhydrous HBr in acetic acid and oxygen to brominated phenol.

As previously mentioned, product yield, paraselectivity, rate, and selectivity to brominated products may be surprisingly improved by using a mixture of Group IV–VIII transition metal catalysts. For example, a vanadium compound catalyst will improve the performance of a molybdenum or tungsten-based catalyst when added thereto. Examples 16–17 illustrate the use of a mixture of bis(acetylacetonate)oxovanadium (VO(acac)$_2$) and sodium molybdenum oxide dihydrate (NaMoO$_4$.2H$_2$O) or a mixture of bis(acetylacetonate)oxovanadium (VO(acac)$_2$) and tungstic acid (H$_2$WO$_4$.xH$_2$O) to catalyze the oxybromination of phenol with anhydrous HBr/O$_2$ in a solvent. However, the invention is not limited to mixtures of these particular catalysts, as one of skill would know.

EXAMPLE 16

The procedure of Example 12 was followed except that 0.026 g (0.1 mmol) of VO(acac)$_2$ and 0.155 g (0.7 mmol) of NaMoO$_4$.2H$_2$O were added as catalysts. The results are found in Table III.

EXAMPLE 17

The procedure of Example 12 was followed except 0.026 g (0.1 mmol) of VO(acac)$_2$ and 0.188 g (0.7 mmol) of H$_2$WO$_4$.xH$_2$O were added as catalysts. The results are found in Table III.

TABLE III

Mixture of Catalysts
Catalytic Bromination of Phenol with Anhydrous HBr/O$_2$ in Acetic Acid

| Example | First Catalyst | Second Catalyst | Yield of BrC$_6$H$_4$OH, % | Selectivity on BrC$_6$H$_4$OH, % | Rate, mol/L · h | Para-selectivity, % | Mono-selectivity, % |
|---|---|---|---|---|---|---|---|
| 16 | VO(acac)$_2$ (0.026) | NaMoO$_4$.2H$_2$O (0.155) | 47.3 | 99.2 | 0.66 | 90.4 | 100 |
| 17 | VO(acac)$_2$ (0.026) | H$_2$WO$_4$.xH$_2$O (0.188) | 55.6 | 96.4 | 0.77 | 90.3 | 100 |

When compared with the results of Example 12 found in Table II, the results of Example 18 shown in Table III show that the addition of the vanadium compound catalyst to the molybdenum compound catalyst significantly increased the paraselectivity of the reaction by about 7%. Furthermore, the selectivity to brominated products increased to 99.2 %, and the yield of brominated products more than doubled, as did the rate of the reaction. Comparing the results of Example 13 shown in Table II with those of Example 19 in Table III, one can see that addition of the vanadium compound catalyst to the tungstic acid catalyst increased the paraselectivity of the reaction by about 8% and the selectivity to brominated products by more than 30% (i.e., 99.4%). Furthermore, the yield of brominated products more than tripled, as did the rate of the reaction.

As shown in Examples 18–19, the addition of a nitrate salt to the transition metal catalyst improves the yield and increases the rate when aqueous HBr is used as the brominating agent. When anhydrous HBr in a solvent is used, the selectivity to brominated phenols and para-selectivity also improves, as shown in Examples 20–24.

EXAMPLE 18

A 3-dram vial equipped with a stirring bar was charged with 1.5 g (15.9 mmol) phenol, 1.90 g of aqueous HBr (48 wt %) (11.3 mmol), 1.4 g of acetic acid, and 0.041 g (0.3 mmol) of $NaVO_3$. The vial was sealed with a cap containing a hole to allow for air flow during the reaction and placed in an aluminum block. The block was placed in a standard one gallon Autoclave Engineers autoclave reactor, pressurized to 34.0 atm with air and heated at 100° C. for 1 hour. It was then cooled to room temperature and depressurized. The resulting mixture was analyzed by vapor phase chromatographic analysis. The results are shown in Table IV.

EXAMPLE 19

The procedure of Example 18 was followed except that 0.045 g (0.5 mmol) of $NaNO_3$ was added with the catalyst. The results are shown in Table IV.

EXAMPLE 20

A 3-dram vial equipped with a stirring bar was charged with 1.5 g (15.9 mmol) phenol, 4 g of 30 % solution of HBr (14.8 mmol) in acetic acid, and 0.104 g (0.9 mmol) of $NaVO_3$. The vial was sealed with a cap containing a hole to allow for air flow during the reaction and placed in an aluminum block. The block was placed in a standard one gallon Autoclave Engineers autoclave reactor, pressurized to 34.0 atm with air and heated at 65° C. for 1 hour. It was then cooled to room temperature and depressurized. The resulting mixture was analyzed by vapor phase chromatographic analysis. The results are shown in Table V.

EXAMPLE 21

The procedure of Example 20 was followed except that the catalyst was 0.074 g (0.6 mmol) $NaVO_3$, and 0.044 g (0.5 mmol) of $NaNO_3$ was added to the reaction mixture. The results are shown in Table V.

EXAMPLE 22

The procedure of Example 20 was followed except that the catalyst was 0.089 g (0.35 mmol) of $VO(acac)_2$, and 0.047 g (0.55 mmol) of $NaNO_3$ was added to the reaction mixture. The results are shown in Table V.

EXAMPLE 23

The procedure of Example 20 was followed except that the catalyst was 0.050 g (0.2 mmol) of $FeBr_2$, and 0.044 g (0.5 mmol) of $NaNO_3$ was added to the reaction mixture. The results are shown in Table V.

EXAMPLE 24

The procedure of Example 20 was followed except that the catalyst was 0.067 g (0.25 mmol) of $TiO(acac)_2$, and 0.043 g (0.5 mmol) of $NaNO_3$ was added to the reaction mixture. The results are shown in Table V.

TABLE IV

Catalytic Bromination of Phenol with HBr aq/$O_2$ and Nitrate Additive

| Ex | HBr aq, g | Solvent (g) | Catalyst (g) | Additive (g) | Yield of BrPhOH % | Selectivity on BrPhOH, % | Rate mol/L · h | Para-selectivity % | Mono-selectivity % |
|---|---|---|---|---|---|---|---|---|---|
| 18 | 1.90 | $C_2H_5COOH$ (1.4) | $NaVO_3$ (0.041) |  | 1.0 | 100 | 0.03 | 100 | 100 |
| 19 | 1.90 | $C_2H_5COOH$ (1.4) | $NaVO_3$ (0.041) | NaNO3 (0.045) | 47.0 | 97.9 | 1.43 | 86.1 | 100 |

TABLE V

Catalytic Bromination of Phenol with Anhydrous HBr/$O_2$ and Nitrate Additive

| Ex. | Catalyst, (g) | Additive, (g) | Yield of BrPhOH, % | Selectivity on BrPhOH, % | Rate, mol/L · h | Para-selectivity, % | Mono-selectivity, % |
|---|---|---|---|---|---|---|---|
| 20 | $NaVO_3$ (0.104) |  | 44.6 | 92.0 | 1.27 | 87.5 | 98.9 |
| 21 | $NaVO_3$ (0.074) | NaNO3 (0.044) | 85.0 | 94.3 | 2.34 | 93.1 | 97.9 |
| 22 | $VO(acac)_2$ (0.089) | NaNO3 (0.047) | 85.1 | 100 | 2.23 | 93.5 | 98.0 |

TABLE V-continued

Catalytic Bromination of Phenol with Anhydrous HBr/O₂ and Nitrate Additive

| Ex. | Catalyst, (g) | Additive, (g) | Yield of BrPhOH, % | Selectivity on BrPhOH, % | Rate, mol/L · h | Para-selectivity, % | Mono-selectivity, % |
|---|---|---|---|---|---|---|---|
| 23 | FeBr₂ (0.050) | NaNO3 (0.044) | 71.1 | 98.1 | 1.98 | 93.9 | 96.2 |
| 24 | TiO(acac)₂ (0.067) | NaNO3 (0.043) | 73.2 | 96.1 | 2.04 | 93.9 | 97.1 |

Examples 25–27 illustrate that a small amount of water added to the oxybromination reaction mixture when anhydrous HBr is used as the brominating agent in the presence of a Group IV–VIII transition metal compound catalyst results in high monoselectivity and paraselectivity of the products. However, the reaction rate and bromophenol yield decreases.

EXAMPLE 25

A 3-dram vial equipped with a stirring bar was charged with 1.5 g (15.9 mmol) phenol, 4 g of 30 % solution of HBr (14.8 mmol) in acetic acid, and 0.250 g (1.0 mmol) of VO(acac)₂. The vial was sealed with a cap containing a hole to allow for air flow during the reaction and placed in an aluminum block. The block was placed in a standard one gallon Autoclave Engineers autoclave reactor, pressurized to 34.0 atm with air and heated at 100° C. for 2 hours. It was then cooled to room temperature and depressurized. The resulting mixture was analyzed by vapor phase chromatographic analysis. The results are shown in Table VI.

EXAMPLE 26

The procedure of Example 25 was followed except that water was added in the ratio of 1 mole H₂O to 1 mole HBr. The results are found in Table VI.

EXAMPLE 27

The procedure of Example 25 was followed except that water was added in the ratio of 2 moles H₂O to 1 mole HBr. The results are found in Table VI.

TABLE VI

Influence of Water on Catalytic Bromination of Phenol with Anhydrous HBr/O₂ and 1 mmole of Vanadium Catalyst (VO(acac)₂)

| Example | H₂O/HBr | Yield of BrPhOH, % | Selectivity on BrPhOH, % | Rate, mol/L · h | Para-selectivity, % | Mono-selectivity, % |
|---|---|---|---|---|---|---|
| 25 | 0 | 43.5 | 93.7 | 1.23 | 89.8 | 99.1 |
| 26 | 1 | 32.0 | 94.6 | 0.88 | 90.9 | 100 |
| 27 | 2 | 10.0 | 99.1 | 0.27 | 90.3 | 100 |

Examples 28–30 illustrate the oxybromination of o-cresol with aqueous HBr in acetic acid and air in the presence of a compound of a Group IV–VIII transition metal as the catalyst. The monoselectivity was 100% and the paraselectivity was greater than 90%.

EXAMPLE 28

A 3-dram vial equipped with a stirring bar was charged with 1.75 g (16.2 mmol) o-cresol, 2 g of aqueous HBr (48 wt %) (11.8 mmol), 1.25 g of acetic acid, and 0.1 g (0.4 mmol) of VO(acac)₂. The vial was sealed with a cap containing a hole to allow for air flow during the reaction and placed in an aluminum block. The block was placed in a standard one gallon Autoclave Engineers autoclave reactor, pressurized to 34.0 atm with air and heated at 100° C. for 1 hour. It was then cooled to room temperature and depressurized. The resulting mixture was analyzed by vapor phase chromatographic analysis. The results are shown in Table VII.

EXAMPLE 29

The procedure of Example 28 was followed except that 0.225 g (0.9 mmol) of VO(acac)₂ was added as the catalyst. The results are shown in Table VII.

EXAMPLE 30

The procedure of Example 28 was followed except that 0.35 g (1.4 mmol) of VO(acac)₂ was added as the catalyst. The results are shown in Table VII.

TABLE VII

Bromination of o-Cresol with HBr aq/O₂ in the Presence of Vanadium Catalyst

| Example | Catalyst VO(acac)₂, g | Yield of bromocresols, % | Rate, mol/L · h | Para-selectivity, % | Mono-selectivity, % |
|---|---|---|---|---|---|
| 28 | 0.1 | 15.7 | 0.49 | 90.4 | 100 |
| 29 | 0.225 | 19.7 | 0.61 | 91.4 | 100 |
| 30 | 0.35 | 23.8 | 0.73 | 91.6 | 100 |

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A method for preparing a brominated hydroxyaromatic compound which comprises contacting a hydroxyaromatic compound with oxygen and a bromine compound selected from the group consisting of hydrogen bromide, elemental bromine, ionic bromide salts, and mixtures thereof, in a polar solvent and an acidic medium, in the presence of a catalyst selected from the group of compounds and mixtures of compounds of Group IV–VIII transition metals of the Periodic Table of Elements.

2. The method of claim 1, wherein said Group IV–VIII transition metals are selected from the group consisting of vanadium, titanium, molybdenum, tungsten, and iron.

3. The method of claim 1, wherein said catalyst is selected from the group consisting of sodium metavanadate, bis(acetylacetonate)oxovanadium, bis(acetylacetonate)oxotitanium, sodium molybdenum oxide dihydrate, iron bromide (FeBr$_2$), tungstic acid (H$_2$WO$_4$.xH$_2$O), and mixtures thereof.

4. The method of claim 1, wherein said catalyst comprises a compound of vanadium in the form of a neutral complex, cationic salt, or anionic salt.

5. The method of claim 1, wherein said catalyst comprises a mixture of a compound of vanadium and a compound of molybdenum or tungsten.

6. The method of claim 5, wherein a molar ratio of said compound of vanadium to said compound of molybdenum or tungsten ranging from about 1:0.5 to about 1:6 is employed.

7. The method of claim 1, wherein a nitrate salt is added to said catalyst.

8. The method of claim 7, wherein said nitrate salt is sodium nitrate.

9. The method of claim 7, wherein said catalyst is a compound of vanadium.

10. The method of claim 7, wherein a molar ratio of said nitrate salt to said catalyst ranging from about 1:1 to about 1:4 is employed.

11. The method of claim 1, wherein said acidic medium is anhydrous.

12. The method of claim 11, wherein said bromine compound is anhydrous hydrogen bromide or an anhydrous ionic bromide salt, and wherein water is added to said anhydrous acidic medium, and wherein a molar ratio of water to anhydrous hydrogen bromide or anhydrous ionic bromide salt ranging from about 0.1:1 to about 2:1 is employed.

13. The method of claim 1 wherein the hydroxyaromatic compound has the formula

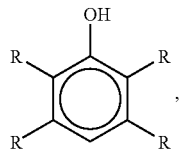

, wherein each R is independently hydrogen or C$_{1-4}$ alkyl.

14. The method of claim 1, wherein said hydroxyaromatic compound is phenol, o-cresol, or m-cresol.

15. The method of claim 1, wherein the bromine compound is hydrogen bromide.

16. The method of claim 1, wherein the bromine compound is elemental bromine having formula Br$_2$.

17. The method of claim 1, wherein said oxygen is provided by air.

18. The method of claim 1, wherein oxygen under pressure is employed.

19. The method of claim 1, wherein flowing oxygen is employed.

20. The method of claim 1, wherein the polar solvent is acetonitrile, dimethyl sulfoxide, chloroform, o-dichlorobenzene, ethyl acetate, water, phenol, o-cresol, m-cresol, propionic acid or acetic acid.

21. The method of claim 1, wherein the polar solvent is acetic acid.

22. The method of claim 1, wherein a temperature in the range of about 20–150° C. is employed.

23. The method of claim 1, wherein said bromine compound is an ionic bromide salt and wherein a molar ratio of said ionic bromide salt to said hydroxyaromatic compound less than 1:1 is employed.

24. The method of claim 1, wherein said bromine compound is elemental bromine and wherein a molar ratio of said elemental bromine to said hydroxyaromatic compound less than 1:2 is employed.

25. The method of claim 1, wherein a molar ratio of said hydroxyaromatic compound to said catalyst ranging from about 1:1 to about 500:1 is employed.

26. A method for preparing 4-bromophenol, 4-bromo-o-cresol or 4-bromo-m-cresol, which comprises contacting phenol, o-cresol or m-cresol, respectively, with air and hydrogen bromide in a polar solvent and an acidic medium, in the presence of a catalyst selected from the group of compounds and mixtures of compounds of Group IV–VIII transition metals of the Periodic Table of Elements.

* * * * *